(12) United States Patent
Motta et al.

(10) Patent No.: US 8,791,287 B2
(45) Date of Patent: Jul. 29, 2014

(54) PROCESS FOR THE SYNTHESIS OF TAPENTADOL AND INTERMEDIATES THEREOF

(75) Inventors: Giuseppe Motta, Rescaldina (IT); Domenico Vergani, Biassono (IT); Giorgio Bertolini, Sesto San Giovanni (IT); Nicola Landoni, Legnano (IT)

(73) Assignee: Euticals S.p.A., Milan (IT)

( * ) Notice: Subject to any disclaimer, the term of this patent is extended or adjusted under 35 U.S.C. 154(b) by 0 days.

(21) Appl. No.: 13/807,356

(22) PCT Filed: Jun. 20, 2011

(86) PCT No.: PCT/IB2011/052685
§ 371 (c)(1),
(2), (4) Date: Dec. 28, 2012

(87) PCT Pub. No.: WO2012/001571
PCT Pub. Date: Jan. 5, 2012

(65) Prior Publication Data
US 2013/0178644 A1    Jul. 11, 2013

(30) Foreign Application Priority Data

Jul. 2, 2010   (IT) ............................... MI2010A1224

(51) Int. Cl.
*C07C 69/76*   (2006.01)
(52) U.S. Cl.
USPC ......................................................... 560/85
(58) Field of Classification Search
CPC .......... C07C 69/80; C07C 67/08; C08K 5/12; A61K 31/195; C07B 2200/07; C07B 57/00
USPC ......................................................... 560/85
See application file for complete search history.

(56) References Cited

U.S. PATENT DOCUMENTS

| 3,888,901 A | 6/1975 | Allen et al. |
| 4,269,833 A * | 5/1981 | Treiber et al. ............ 514/211.01 |
| 7,417,170 B2 | 8/2008 | Hell et al. |

FOREIGN PATENT DOCUMENTS

| EP | 0013749 | 8/1980 |
| EP | 0693475 | 7/1995 |
| WO | WO2008/012047 | 1/2008 |
| WO | WO2008012047 A1 * | 1/2008 |

OTHER PUBLICATIONS

International Search Report for PCT/IB2011/052685 of Sep. 15, 2011.

Italian Search Report for ITMI20101224 of Jan. 18, 2011.

* cited by examiner

Primary Examiner — Brandon Fetterolf
Assistant Examiner — Blaine G Doletski
(74) Attorney, Agent, or Firm — Hueschen and Sage (57) ABSTRACT

The object of the present invention is a new process for the synthesis of tapentadol, both as free base and in hydrochloride form, which comprises the step of alkylation of the ketone (VII) to yield the compound (VIII), as reported in Diagram 1, with high stereoselectivity due to the presence of the benzyl group as substituent of the amino group. It was surprisingly found that this substitution shifts the keto-enol equilibrium towards the desired enantiomer and amplifies the capacity of the stereocenter present in the compound (VII) to orient the nucleophilic addition of the organometallic compound at the carbonyl towards the desired stereoisomer. This substitution thus allows obtaining a considerable increase of the yields in this step, and consequently allows significantly increasing the overall yield of the entire tapentadol synthesis process.
A further object of the present invention is constituted by the tapentadol free base in solid form, obtainable by means of the process of the invention.
Still another object of the invention is represented by the crystalline forms I and II of the tapentadol free base.
A further object of the present invention is the mixture of the crystalline forms I and II of the tapentadol free base.

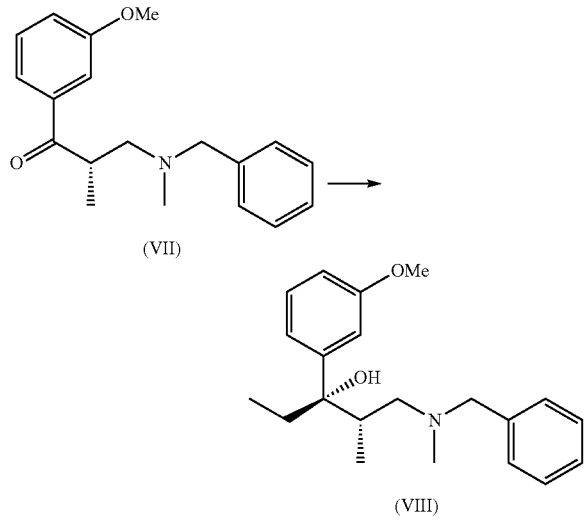

Scheme 1

38 Claims, 5 Drawing Sheets

Figure 1

PXRD of the crystalline form I

Figure 2

FT-IR of the crystalline form I

Figure 3

DSC of the crystalline form I

[Termo analisi = Thermal Analysis]

Figure 4

PXRD of the crystalline form II

Figure 5

FT-IR of the crystalline form II

Figure 6

DSC of the crystalline form II

PROCESS FOR THE SYNTHESIS OF TAPENTADOL AND INTERMEDIATES THEREOF

The object of the present invention is a new process for the synthesis of tapentadol, both as free base and in hydrochloride form, which comprises the step of alkylation of the ketone (VII) to yield the compound (VIII), as reported in Scheme 1, with high stereoselectivity due to the presence of the benzyl group as substituent of the amino group. Indeed, it was surprisingly found that this substitution shifts the keto-enol equilibrium towards the desired enantiomer and amplifies the capacity of the stereocenter present in the compound (VII) to orient the nucleophilic addition of the organometallic compound at the carbonyl towards the desired stereoisomer. This solution, therefore, allows obtaining a considerable increase of the yield in this step, and consequently allows significantly increasing the overall yield of the entire tapentadol synthesis process.

Scheme 1

A further object of the present invention is constituted by the tapentadol free base in solid form obtainable by means of the process of the invention.

Still another object of the invention is represented by the crystalline forms I and II of the tapentadol free base.

A further object of the present invention is constituted by the mixture of the crystalline forms I and II of the tapentadol free base.

STATE OF THE ART

Tapentadol, i.e. 3-[(1R,2R)-3-(dimethylamino)-1-ethyl-2-methylpropyl]phenol, having the formula reported hereinbelow:

is an analgesic with agonist central action for the receptors μ of the opioids and inhibitor of the re-uptake of noradrenaline, used for the treatment of moderate-to-grave acute pain.

Derivates with structure similar to tapentadol are described in the literature.

U.S. Pat. No. 7,417,170 is relative to a process for synthesizing, with good yields, the 3-aryl-butyl-amino compounds by means of the elimination of the tertiary alcoholic function from 4-amino-2-aryl-butan-2-ol compounds.

EP693475 describes the synthesis of 1-phenyl-3-dimethylamino-propane compounds equipped with pharmacological activity.

U.S. Pat. No. 3,888,901 regards the synthesis of compounds of the 3-alkyl-3-substituted-benzoyl)propionitrile class, starting from phenyl alkyl ketones via Mannich reaction.

WO2008012047 reports the synthesis of tapentadol, starting from 3-bromoanisole which, via organic lithium, is transformed into 3-methoxypropiophenone. A Mannich reaction is carried out on this intermediate which leads to the racemic intermediate reported hereinbelow:

This racemic intermediate is subjected to an enantiomeric separation by means of reaction with the chiral (2R,3R)-O, O'-dibenzoyltartaric acid in order to obtain the preferred enantiomer reported hereinbelow:

The resolved enantiomer is then alkylated at the carbonyl by means of reaction with ethylmagnesium bromide and finally the product of this reaction is hydrogenated and subsequently demethylated.

During the alkylation reaction, the formation of two diastereoisomers is verified; the removal of the undesired isomer (1S,2R) involves the need for crystallization in conditions which lead to the loss of a high percentage of product.

Therefore, the development of a new process capable of minimizing the formation of the undesired stereoisomer during the reaction of alkylation of the carbonyl group would allow obtaining a considerable increase of the overall process yields.

DESCRIPTION OF THE INVENTION

The object of the present invention is a new process for the synthesis of tapentadol, both as free base and in hydrochloride form, below indicated as "tapentadol", which comprises the step of alkylation of the ketone (VII) to yield the compound (VIII), as reported in Scheme 1, with high stereo selectivity due to the presence of the benzyl group as a substituent of the amino group. This substitution shifts the keto-enol equilibrium towards the desired enantiomer and amplifies the capacity of the stereocenter present to orient the nucleophilic addition of the reagent at the carbonyl, allowing the obtainment of a considerable increase of the overall process yields.

Scheme 1

The synthethic scheme for obtaining tapentadol according to the present invention preferably starts from the compound 1-(3-methoxyphenyl)propan-1-one of formula (II):

Said compound (II) is condensed with benzylmethylamine to form the compound (V), as reported in Scheme 2 hereinbelow.

Scheme 2

Such reaction, known as a Mannich condensation, is conducted in a suitable organic solvent (J. March, Advanced Organic Chemistry, 3 and Wiley-Interscience: 1985, New York, pp. 800-802), incorporated herein for reference. The benzylmethyl immonium ion can be previously synthesized or directly synthesized in the reaction mixture. In order to form the benzylmethyl immonium ion, formaldehyde can be used, or a precursor thereof such as 1,3,5-trioxane or paraformaldehyde, and benzylmethylamine or bisbenzylmethylaminomethane and a suitable acid. The following can be used as solvent: polar aprotic solvents, such as acetonitrile, non-polar aprotic solvents, such as toluene, aliphatic alcohols or organic acid anhydrides. When the anhydride of an organic acid is used as a solvent, it is not necessary to add other acids to make the reaction proceed. The reaction temperature can be comprised between 0° C. and the boiling temperature of the solvent.

In a preferred embodiment, the reaction conditions provide for the use of acetic anhydride as solvent and/or a temperature comprised between 50 and 80° C.

In U.S. Pat. No. 429,833, said reaction between the previously synthesized benzylmethyl immonium ion and the 3-methoxyacetophenone substrate is carried out in acetonitrile.

The compound (V), obtained as a mixture of stereoisomers, in solution interconverts by means of the tautomeric form of the carbonyl that is generated via keto-enol equilibrium, as reported in Scheme 3.

Scheme 3

The equilibrium can be shifted towards the enantiomer of interest by making the latter precipitate as a chiral acid salt (HX*), as reported in Scheme 4, from a suitable polar solvent or from a mixture of polar solvents.

Scheme 4

(VI) → (VII)

The solvents preferably used for this separation are selected from among the following: water, aliphatic ketones, aliphatic alcohols or another polar solvent used separately or in a mixture with other polar solvents. The preferred alcohols are methanol, ethanol, 1-propanol, 2-propanol and the preferred ketone is acetone. Preferably, a mixture of methanol and isopropanol is used. As chiral acids, the following can be used: D(−) mandelic acid, D(−) 2-chloromandelic acid, D(−) tartaric acid, (2R,3R)-O,O'-dibenzoyl tartaric acid, preferably D(−) mandelic acid. The resolved enantiomer salt is then suspended in a mixture of water and a suitable organic solvent. With the addition of an aqueous basic solution, the stereoisomer (VII) is liberated from the salt (VI), in free base form. The compound (VII) is then extracted from the organic solvent, from which it can be recovered via evaporation of the solvent, while the chiral acid salt with the base remains in water and can also be recovered. According to the present invention, the bases are preferably selected from among an ammonium hydroxide, an alkaline metal hydroxide or alkaline-earth metal hydroxide, more preferably sodium hydroxide or potassium hydroxide. The organic solvent is preferably selected from among toluene, methyl tert-butyl ether (MTBE), methyl iso-butyl ketone (MiBK) and 2-methyltetrahydrofuran (MTHF).

Then, a further object of the present invention is constituted by a new process for the synthesis of tapentadol which uses the stereoisomer (VII) obtained by means of the step of resolution of the racemic mixture (V). Said step of resolution of the racemic mixture (V) comprises the steps of:

a') reaction of the racemic mixture of the compound (V) with a chiral acid (HX*) in a polar solvent or mixture of polar solvents and subsequent precipitation of the chiral salt (VI);

b') treatment of the chiral salt (VI) with an aqueous basic solution to yield the compound (VII);

c') subsequent extraction of the compound (VII) thus obtained with an organic solvent.

A further object of the present invention is then constituted by the reaction of alkylation of the compound (VII), obtained by means of the above-described step of resolution of the racemic mixture (V), to yield the compound (VIII) by means of reaction with an organometallic compound, i.e. an ethyl metal halide, as represented in Scheme 1.

Scheme 1

(VII)

(VIII)

This step proceeds with high stereoselectivity due to the presence of the benzyl group as substituent of the amino group. Indeed, it was surprisingly found that this substitution shifts the keto-enol equilibrium towards the desired enantiomer and amplifies the capacity of the stereocenter present in the compound (VII) to orient the nucleophilic addition of the organometallic compound at the carbonyl towards the desired stereoisomer. The reaction in fact proceeds with an enantiomeric excess (ee) greater than 99%. Therefore, this substitution allows obtaining, with respect to the known syntheses reported in the literature, a considerable increase of the yields in this step, and consequently allows significantly increasing the overall yield of the entire tapentadol synthesis process.

The organometallic compound, i.e. the ethyl metal halide, can be purchased or synthesized in situ by means of reaction of the shavings of the metal with an ethyl halide in a suitable organic solvent. Added dropwise to the obtained organometallic solution is the compound (VIII) dissolved in an organic solvent, which does not have to be the same one used for the synthesis of the organometallic compound. The reaction temperature is maintained between 0° C. and the boiling temperature of the solvent, preferably between 10 and 30° C. The metals used are preferably selected between zinc and magnesium while the preferred ethyl halide is bromide; according a particularly preferred aspect, the organometallic compound is ethylmagnesium bromide. Preferably, 1 to 5 equivalents of organometallic compounds are used with respect to the compound (VIII).

Upon completed reaction, the mixture is poured into an acidic aqueous solution, from which the compound (VIII) is extracted with organic solvent. In order to acidify the aqueous phase, an organic acid, an inorganic acid or a salt which, dissolved in water, yields an acidic pH, can be used. Preferably, ammonium hydrogen sulfate is used. The compound (VIII) can be used as is in the subsequent step or purified by means of the methods known in the art, preferably via crystallization.

The compound (VIII) is transformed into the compound (X) by means of the activation of the hydroxyl and subsequent reduction and hydrolysis, as represented in Scheme 5.

Scheme 5

1 to 5 equivalents of an organic acid halide or anhydride with respect to the compound (VIII) are added to a solution of the compound (VIII), obtained directly from the preceding step, or by dissolving the crystallized product in a suitable solvent. The organic acid halide or anhydride is preferably a halide or anhydride of a substituted or non-substituted aromatic or aliphatic organic acid, preferably a $C_1$-$C_5$ alkyl acid, optionally substituted with 1-3 halogen atoms; a benzoic acid or a phenylacetic acid, optionally substituted with 1 to 3 halogen atoms, alkyl groups and/or carboxyl groups; $C_1$-$C_6$ dicarboxylic acids and their $C_1$-$C_4$ aliphatic esters. Preferably, said halides or anhydrides of the organic acid are halides or anhydrides of acetic acid, phenylacetic acid, chloroacetic acid, trifluoroacetic acid, benzoic acid, chlorobenzoic acid, phthalic acid, succinic acid, oxalic acid or $C_1$-$C_4$ aliphatic monoesters of oxalic acid or mixed formic acid anhydrides, still more preferably trifluoroacetic acid.

The reaction is allowed to proceed until there is complete esterification of the benzilic hydroxyl.

Alternatively, this esterification reaction can be carried out by adding to the compound (VIII) a suitable organic acid and a dehydrating agent, preferably DCC (dicyclohexylcarbodiimide), HOBT (hydroxybenzotriazole), EDC (1-ethyl-3-(3-dimethylaminopropyl)carbodiimide) or T3P (2-propanefosfonic acid), in a suitable solvent.

In Scheme 5, R can have the following meanings:
$C_1$-$C_5$ alkyl, optionally substituted with 1-3 halogen atoms, or with a carboxyl group, possibly esterified with $C_1$-$C_4$ aliphatic alcohols, or,
phenyl or benzyl, optionally substituted with 1-3 halogen atoms, with alkyl and/or carboxyl groups.
Preferably, R is: H, $CH_3$, $CH_2Cl$, $CF_3$, $CH_2CH_2COOH$, $COOR^1$ wherein $R^1$ is H or $C_1$-$C_4$ alkyl, phenyl radical, chlorophenyl radical, o-carboxyphenyl radical.

A catalyst is then added to the reaction mixture, said catalyst preferably being palladium on carbon, and this is hydrogenated at a pressure comprised between 1 and 100 bar and/or a temperature comprised between 0 and 100° C.

Once the hydrogenation has terminated, the catalyst is removed via filtration, the solution is concentrated and an aqueous solution is added of a base for hydrolyzing the anilide. Once the hydrolysis has terminated, the compound (X) is extracted with a water-immiscible solvent and obtained as an oil by concentration.

The compound (X) can be used as is in the subsequent reaction or it can be crystallized with the addition of an appropriate insolubilizing solvent. Said insolubilizing solvent is preferably an aromatic or aliphatic hydrocarbon, more preferably n-hexane, cyclohexane, heptane, petroleum ether, toluene, which can be added before or after the concentration, preferably after the concentration.

Alternatively, the compound (X) can be precipitated as a salt via the addition of an acid to the extraction solution. In this case, it is preferably precipitated as hydrochloride by bubbling HCl gas into the extraction solution.

The compound (X) is finally transformed into tapentadol by means of methylation of the amine to yield the compound (XI) and release of the methyl ether, as represented in Scheme 6.

Scheme 6

The methylation of the amine can be carried out by using a methylating agent preferably in the presence of a base, or by means of a reductive methylation, preferably by means of reductive methylation using formaldehyde, or a precursor thereof, and a suitable reducing agent.

Said methylating agent can preferably be selected from among methyl iodide, methyl bromide, methyl chloride, dimethylsulfate, a sulfonic or benzenesulfonic acid methyl ester, either substituted or non-substituted.

Said base can be an organic base, preferably triethylamine or diisopropylamine, or an inorganic base, preferably selected from among an alkaline-earth metal or alkaline metal hydroxide, carbonate or bicarbonate.

Said reducing agent can be preferably selected from among a hydride, hydrogen or hydrogen donor, preferably in the presence of a catalyst.

Preferably, the reductive methylation reaction is carried out by using formaldehyde and formic acid, i.e. by means of Eschweiler-Clarke reaction [Organic Reactions 5, 301 (1949), incorporated herein for reference].

The process according to the present invention further comprises the reaction of O-demethylation of the compound (XI) to yield the tapentadol free base, which can be in oil form or in solid form.

It has now been surprisingly found that from the intermediate (XI), obtained with the process of the invention, it is possible to obtain the tapentadol free base which has a greater level of purity than that obtained by means of methods known in the art.

Therefore, a further object of the present invention is constituted by the tapentadol free base which has a purity level greater than 99% by weight.

Due to this high purity level, the tapentadol free base can be crystallized, unlike what occurred in the preceding art.

Said crystallization can be obtained by dissolving the tapentadol free base in an aprotic polar solvent, preferably ethyl acetate, preferably by heating to a temperature comprised between 30° C. and the boiling temperature of the solvent, more preferably about 50° C., and then by cooling the solution thus obtained.

Alternatively, said crystallization can be obtained by dissolving the tapentadol free base in an aprotic polar solvent, preferably ethyl acetate, preferably by heating to a temperature comprised between 30° C. and the boiling temperature of the solvent, more preferably to about 50° C., and by adding the solution thus obtained dropwise into an insolubilizing solvent.

Said insolubilizing solvent is preferably an aromatic or aliphatic hydrocarbon, more preferably n-hexane, cyclohexane, heptane, petroleum ether, toluene, more preferably heptane.

Said insolubilizing solvent, preferably heptane, can be used hot or cold.

According to the invention, with the term "hot" it is intended that the insolubilizing solvent, preferably heptane, has a temperature preferably comprised between 30 and 90° C., more preferably about 50° C.

According to the invention, with the term "cold" it is intended that the insolubilizing solvent, preferably heptane, has a temperature preferably comprised between −10 and 10° C., more preferably about 0° C.

Alternatively, said crystallization can be obtained via solidification of the oil, preferably at ambient temperature.

A further object of the present invention is therefore constituted by the tapentadol free base in solid form obtainable by means of the process of the invention.

A further object of the invention is the crystalline form I of the tapentadol free base.

Said crystalline form I is preferably obtained by dissolving the tapentadol free base in an aprotic polar solvent, preferably ethyl acetate, preferably by heating to a temperature comprised between 30° C. and the boiling temperature of the solvent, more preferably at about 50° C. and by adding the solution thus obtained dropwise into an insolubilizing solution, preferably heptane, more preferably cold heptane.

Figure 1:
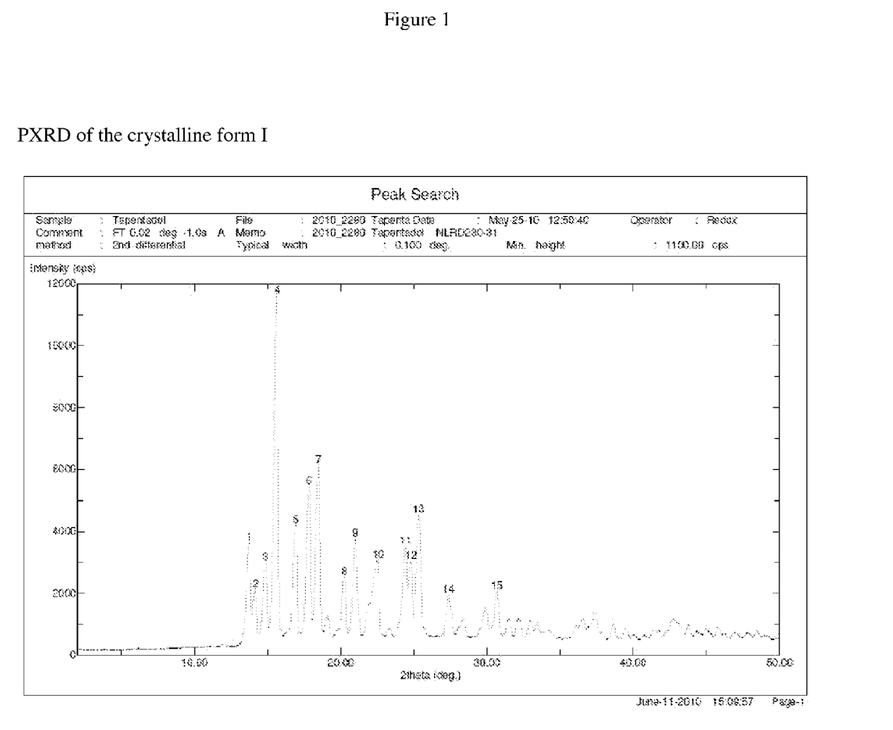
FIG. 1 shows the PXRD diffractogram for crystalline form I of the tapentadol free base.
Figure 2:
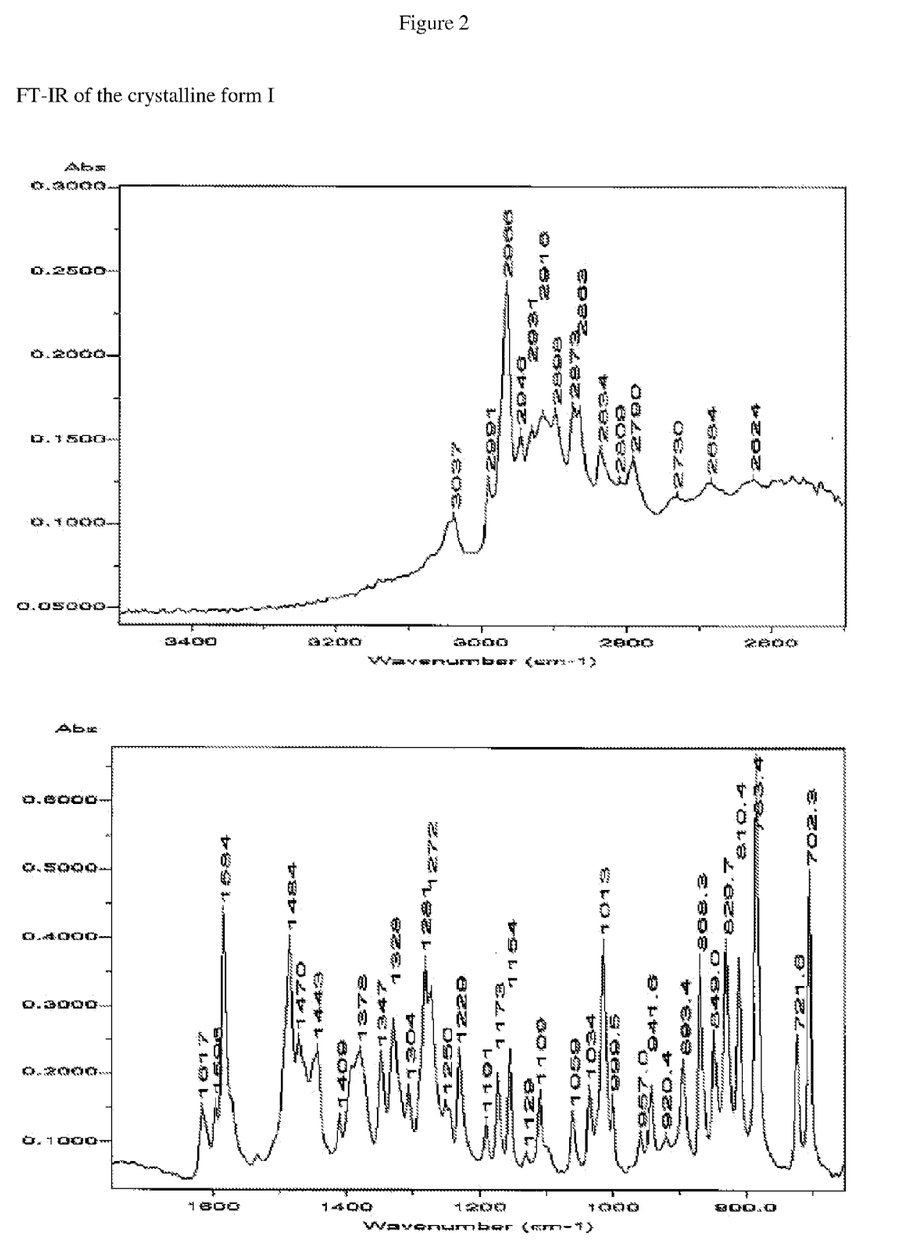
FIG. 2 shows the FT-IR profile for crystalline form I of the tapentadol free base.
Figure 3:
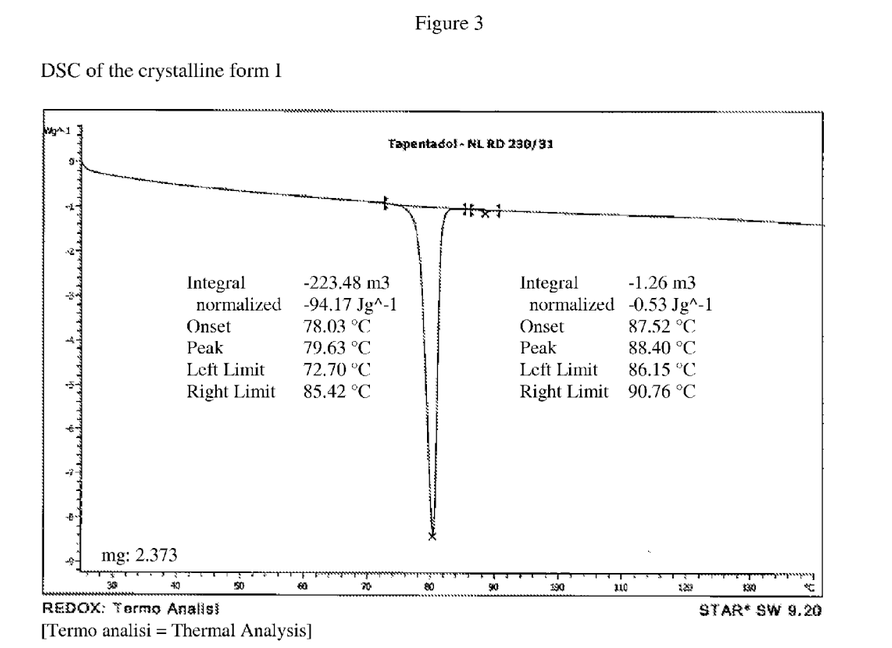
FIG. 3 shows the DSC profile for crystalline form I of the tapentadol free base.

Said crystalline form I is preferably characterized by a PXRD diffractogram as reported in FIG. 1 and/or by a FT-IR profile as reported in FIG. 2 and/or by a DSC profile as reported in FIG. 3.

More preferably, said crystalline form I is characterized by a PXRD diffractogram that comprises the following main peaks: 13.76, 15.62, 16.94, 18.46, 21.02, 30.7 2theta, and/or by a FT-IR profile that comprises the following main peaks: 2979, 2952, 2867, 1457, 1333, 1266, 1094, 816 cm$^{-1}$, and/or by a DSC profile which shows a peak at 79.63° C. with an onset at 78.03° C.

A further object of the invention is the crystalline form II of the tapentadol free base.

Said crystalline form II is preferably obtained by dissolving the tapentadol free base in an aprotic polar solvent, preferably ethyl acetate, preferably by heating to a temperature comprised between 30° C. and the boiling temperature of the solvent, more preferably to about 50° C. and adding the solution thus obtained dropwise into an insolubilizing solution, more preferably hot heptane.

Figure 4:
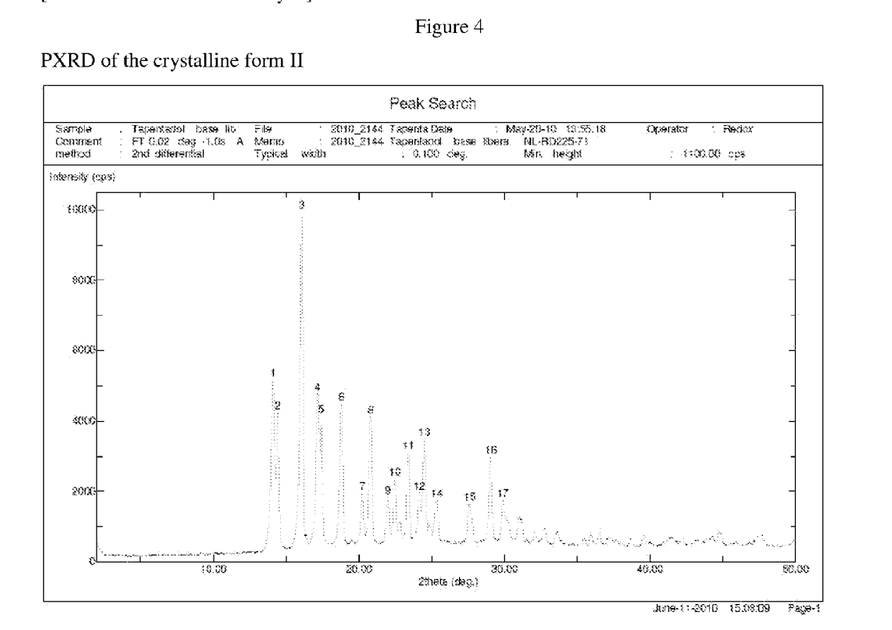
FIG. 4 shows the PXRD diffractogram for crystalline form II of the tapentadol free base.
Figure 5:
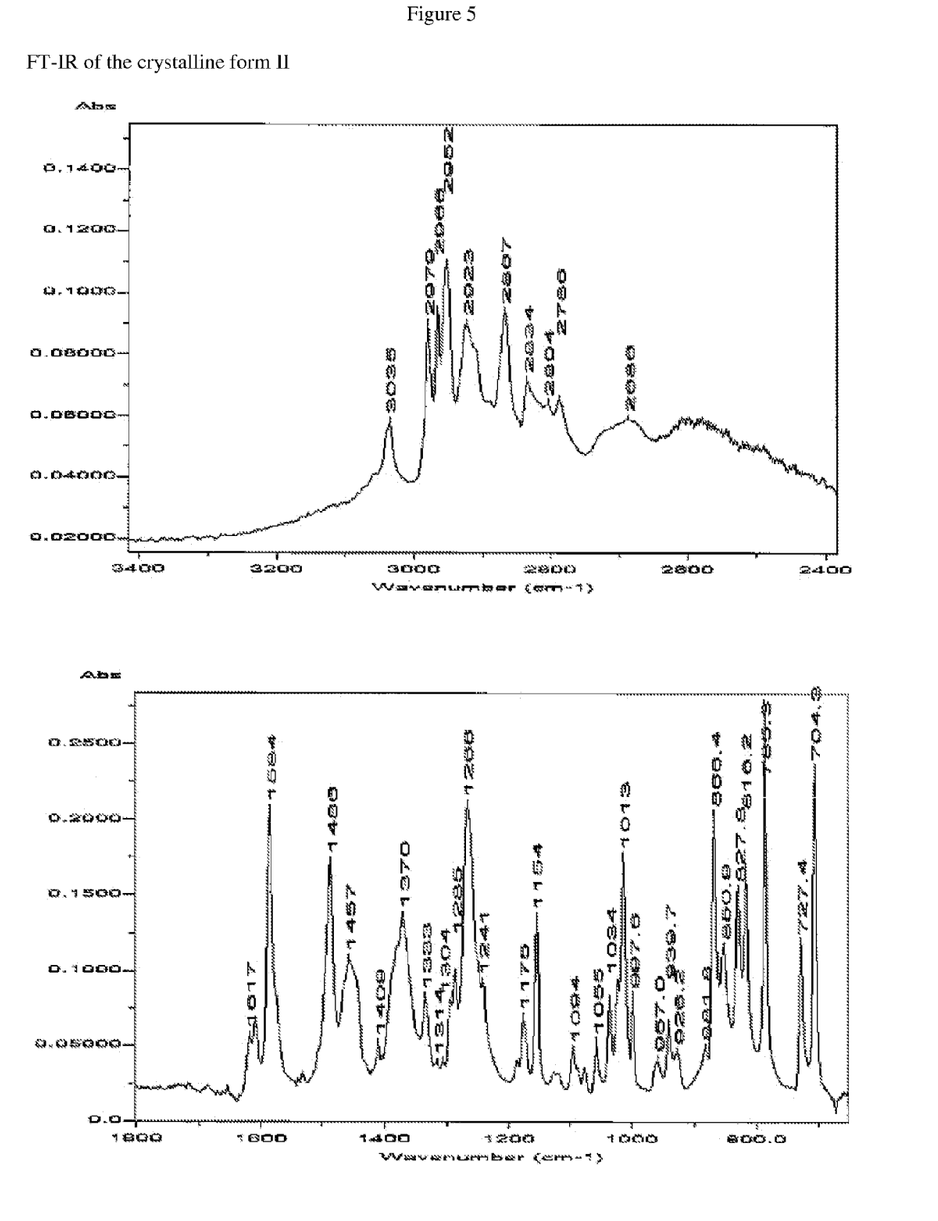
FIG. 5 shows the FT-IR profile for crystalline form II of the tapentadol free base.
Figure 6:
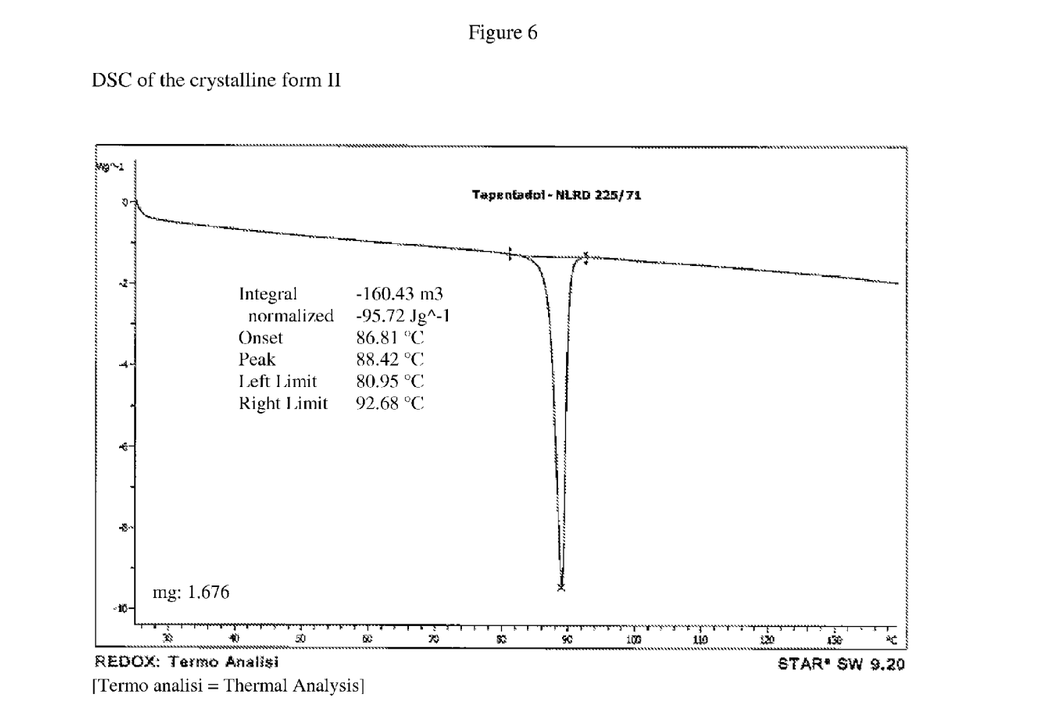
FIG. 6 show the DSC profile for crystalline form II of the tapentadol free base.

Said crystalline form II is preferably characterized by a PXRD diffractogram as reported in FIG. 4 and/or by a FT-IR profile as reported in FIG. 5 and/or by a DSC profile as reported in FIG. 6.

More preferably, said crystalline form II is characterized by a PXRD diffractogram that comprises the following main peaks: 14.44, 16.08, 17.18, 17.42, 18.82, 20.8 2theta, and/or by a FT-IR profile that comprises the following main peaks: 2991, 2898, 1617, 1328, 1281, 1229, 1173, 893 cm$^{-1}$, and/or by a DSC profile which shows a peak at 88.42° C. with an onset at 86.81° C.

Still another object of the invention is a mixture of the two crystalline forms I and II of the tapentadol free base.

A further object of the present invention is represented by the compounds of formula:

(VII')

(VII')

wherein R is: $C_1$-$C_5$ alkyl, optionally substituted with 1-3 halogen atoms, or with a carboxyl group, optionally esterified with $C_1$-$C_4$ aliphatic alcohols; or phenyl or benzyl, optionally substituted with 1-3 halogen atoms, with alkyl and/or carboxyl groups;

(VI'):

(VI')

wherein R is: $C_1$-$C_5$ alkyl, optionally substituted with 1-3 halogen atoms, or with a carboxyl group, possibly esterified with $C_1$-$C_4$ aliphatic alcohols; or phenyl or benzyl, optionally substituted with 1-3 halogen atoms, with alkyl and/or carboxyl groups and in which HX* is an optically active acid;

(VIII):

(VIII)

(IX):

(IX)

wherein R is:
C$_1$-C$_5$ alkyl, optionally substituted with 1-3 halogen atoms, or with a carboxyl group, possibly esterified with C$_1$-C$_4$ aliphatic alcohols; or phenyl or benzyl, optionally substituted with 1-3 halogen atoms, with alkyl and/or carboxyl groups;

preferably R is: H, CH$_3$, CH$_2$Cl, CF$_3$, CH$_2$CH$_2$COOH, COOR$^1$ wherein R$^1$ is H or C$_1$-C$_4$ alkyl, phenyl radical, chlorophenyl radical, o-carboxyphenyl radical.

(X):

(X)

These compounds are obtained as intermediates in the tapentadol synthesis process according to the present invention.

The object of the present invention is also the use of one or all said compounds (VII'), (VI'), (VIII), (IX), (X) as intermediates in the tapentadol synthesis process according to the present invention.

EXAMPLE 1

Mannich Reaction

Synthesis of 3-(benzyl-methyl-amino)-2-methyl-1-(3-methoxy-phenyl)-propan-1-one (V)

In a four-neck 1 L flask equipped with reflux, thermometer and mechanical stirrer, the following are loaded: 95% w/w paraformaldehyde (19.2 g, 0.638 moles) and acetonitrile (300 mL/234 g, 5.70 moles). The mixture is cooled to a temperature less than 10° C., then the following are loaded: 97% w/w N-benzylmethylamine (77.3 g, 0.638 moles), 36% HCl (70.9 g/60.0 mL, 0.70 moles). Finally, 99.7% 1-(3-methoxy-phenyl)-propan-1-one (100 g, 0.608 moles) is added. The reaction mixture is heated at 65±5° C. for 20-24 hours and the conversion is verified by means of HPLC. Upon completed reaction, the solution is concentrated under vacuum at 35-50° C. and 200-300 mL of solvent is collected. Added to the mixture are: toluene (100 ml) and purified water (200 ml), and stirring proceeds for 30 minutes at ambient temperature. The phases are separated and toluene (200 ml) is added to the aqueous phase. The pH is brought to 11-13 with 28% NaOH (about 105 g). The mixture is stirred for 30 minutes and the phases separated. The toluene phase is distilled under vacuum at 35-45° C. IPA (100 mL) is then added and the residue solvent is distilled.

201 g of pale yellow oil are obtained, 97% yield with a HPLC purity of 87%. The oil thus obtained is used as is for the subsequent step.

EXAMPLE 2

Resolution

Synthesis of (S)-3-(benzyl-methylamino)-2-methyl-1-(3-methoxy-phenyl)-propan-1-one (VII)

In a four-neck 1 L flask, the following are loaded: 3-(benzyl-methyl-amino)-2-methyl-1-(3-methoxy-phenyl)-propan-1-one from the preceding step, R(−) mandelic acid (93 g, 0.608 moles) and IPA (650 mL). The suspension is stirred at 15-25° C. until complete dissolution is attained. The reaction is stirred at 15±5° C. for 48 hours and then at 4±4° C. for 2 hours. The solid is filtered and the suspension washed with 3×60 mL of IPA. The product is dried under vacuum at 40-45° C. 150 g of colorless solid (98.2% ee S enantiomer) are obtained. The product is suspended in 450 mL of water, and under stirring the pH is brought to 10-12 with 28% NaOH (about 36.0 g). Toluene (450 mL) is then loaded. The phases are stirred for 30-60 minutes, then they are separated. The organic phase, after anhydrification, is filtered and then concentration under vacuum at 35-45° C. until a colorless oil is obtained.

98 g of (S)-3-benzyl-methyl-amino)-2-methyl-1-(3-methoxy-phenyl)-propan-1-one are obtained as a colorless oil.

EXAMPLE 3

Synthesis of (2S,3R)-1-(benzylmethylamino)-3-(3-methoxyphenyl)-2-methyl-3-pentanol (VIII)

In a four-neck 500 mL flask, equipped with reflux, thermometer and mechanical stirred, in nitrogen atmosphere, a solution of ethylmagnesium bromide (125 mL, 1M in Me-THF, 0.125 mol) is loaded. A solution of (S)-3-(Benzyl-methyl-amino)-1-(3-methoxyphenyl)-2-methylpropan-1-one (18.5 g, 0.0623 mol) in 10 mL of Me-THF is added dropwise to this solution at 10-35° C. in about 60 minutes. The mixture is stirred at 25-30° C. for 2-3 hours. The conversion is verified by means of HPLC (≥99%). The reaction is cooled to 4° C., then washed by slowly adding: a 10% solution of ammonium hydrogen sulfate (75 mL). The organic phase is concentrated to oil under vacuum at 45-60° C.

A pale yellow oil is obtained which is used as is for the subsequent step.

EXAMPLE 4

Synthesis of (2R,3R)-3-(3-methoxyphenyl)-N,N,2-trimethylpentan-1-amine 2 hydrochloride (VII)

In 80 mL of Me-THF, the oil obtained in the previous step is dissolved: (2S,3R)-1-(methylbenzylamino)-3-(3-methoxyphenyl)-2-methyl-3-pentanol. Maintaining the temperature <40° C., trifluoroacetic anhydride is added (13.08 g, 0.0623 mol). The mixture is heated to 35-45° C. for 2-3 hours and the conversion verified by means of HPLC control. The mixture is cooled to ambient temperature and anhydride Pd/C (2.0 g) is added in nitrogen atmosphere. The mixture is then placed in hydrogen atmosphere at 3-6 bar for 16-24 hours at a temperature of 20-35° C. and the reaction is considered completed with a compound residue (IX)≤1.0%. The catalyst is filtered and washed with 10 mL of Me-THF. Purified water (30 mL) is added to the solution. The pH is then brought to 10-12 by means of the addition of 28% NaOH. The phases are separated and the organic phase is concentrated to oil under vacuum at 45-50° C. and then it is diluted with heptane (30 mL). Stirring proceeds for 4 hours, a precipitate is formed which is filtered and subsequently washed with the mother liquors and with heptane (10 mL).

The solid is dried under vacuum at 45° C. until constant weight is attained.

The obtained product is a white solid with a yield of 60-80% calculated from the starting compound (VII) (mp=140.6° C., HPLC purity=97%).

EXAMPLE 5

Synthesis of (3R,3R)-[3-(3-methoxyphenyl)-2-methylpentyl]-dimethyl-amine 2 hydrochloride In a four-neck 1 L flask, equipped with reflux, thermometer and mechanical stirrer, the following is loaded: 98% formic acid (2.8 g, 0.06 moles), and this is cooled below 10° C. The following is loaded to the cooled solution: (3R,3R)-3-(3-methoxyphenyl)-2-methyl-pentyl)-methyl-amine (6.1 g, 0.028 moles). To this solution, 37% formaldehyde (2.9 g, 0.036 moles) is loaded. The reaction is stirred and heated to 90-95° C. for 3-4 hours. Upon completed reaction, the mixture is cooled to 20-25° C. and purified water is loaded (30 mL). The pH is brought to 9-10 with 28% NH$_4$OH (about 10 g). The product is extracted with 3-pentanone (30 mL). The organic phase is concentrated to oil under vacuum at 45-50° C., then diluted with 3-pentanone (50 mL) and cooled to 20-25° C. In this solution, the following is bubbled: HCl gas (1.1 g, 0.03 moles), and the resulting suspension is stirred for 2-3 hours. The crystallized product is filtered and finally washed with acetone (2×15 mL). The product is obtained as a crystalline solid with a HPLC purity of 98% (6.5 g, about 90% yield).

EXAMPLE 6

Synthesis of (1R,2R)-3-(3-dimethylamino-1-ethyl-2-methoxypropyl)-phenol (tapentadol)

In 28 mL of methanesulfonic acid, (2R,3R)-3-(3-methoxyphenyl)-N,N,2-trimethylpentan-1-amine HCl (6.0 g, 0.022 moles) is dissolved, and methionine (4.7 g, 0.031 moles) is added to the solution. The reaction is stirred at the temperature of 75-80° C. for 16-20 hours. It is then cooled to 15-25° C. and the following is added: purified water (20 mL), slowly at this temperature. The pH is brought to the value of 10-11 by means of the addition of 28% NaOH (about 35 mL), maintaining the temperature below 50° C. Then, ethyl acetate (30 mL) is added to the mixture. The mixture is then stirred for 30 minutes and the organic phase is separated. The organic phase, with dark color, is filtered over a silica panel and washed with 30 mL of ethyl acetate. A yellowish transparent solution is obtained. The solvent is removed under vacuum, obtaining about 5.5 g of oil which, left at ambient temperature, solidifies.

EXAMPLE 7

Crystallization of (1R,2R)-3-(3-dimethylamino-1-ethyl-2-methoxypropyl)-phenol

A: from Ethyl Acetate

A part of the product obtained in Example 6 is dissolved in the minimum quantity of ethyl acetate at 50° C. and cooled to ambient temperature, obtaining a solid that is filtered and dried. A solid is obtained which in DSC shows a peak at 79.63° C. with an onset at 78.03° C. and a peak at 88.42° C. with an onset at 86.81° C.

B: from Cold Heptane

A part of the product obtained in Example 6 is dissolved in the minimum quantity of ethyl acetate at 50° C. and added dropwise into 30 ml of heptane at 0° C. The obtained solid is maintained under stirring in suspension, filtered and dried. A solid is obtained which in DSC shows a peak at 79.63° C. with an onset at 78.03° C.

C: from Hot Heptane

A part of the product obtained in Example 6 is dissolved in the minimum quantity of ethyl acetate at 50° C. and added dropwise into 30 ml of heptane at 50° C. The obtained solid is maintained under stirring in suspension 50° C., filtered and dried. A solid is obtained which in DSC shows a peak at 88.42° C. with an onset at 86.81° C.

D: by Solidification of the Oil

A part of the product obtained in Example 6 is maintained at ambient temperature for several days. A solid is obtained which in DSC shows a peak at 79.63° C. with an onset at 78.03° C. and a peak 88.42° C. with an onset at 86.81° C.

EXAMPLE 8

Crystallization of (1R,2R)-3-(3-dimethylamino-1-ethyl-2-methoxypropyl)-phenol hydrochloride Part of the oil obtained in Example 6 is dissolved in 2-butanone (40 mL) at the temperature of 20-25° C. The following are added: purified water (0.3 mL, 0.0167 moles), trimethylchlorosilane (1.2 g). The hydrochloride product precipitates and the suspension is maintained under stirring for 4 hours at the temperature of 20-25° C. Finally, the solid is filtered, and this is dried under vacuum at 30-40° C.

4.2 g of product are obtained with HPLC purity >99.8%. Molar yield: 74.5%.

The invention claimed is:

1. A process for the synthesis of tapentadol comprising alkylation of compound (VII)

(VII)

with an ethyl metal halide in an organic solvent to yield compound (VIII)

(VIII)

wherein the compound of formula (VIII) is further reacted to produce tapentadol.

2. The process according to claim 1, wherein the halide is bromide and the metal is zinc or magnesium.

3. The process according to claim 1, wherein the ethyl metal halide is ethylmagnesium bromide.

4. The process according to claim 2, wherein the ethyl metal halide is used in a quantity between 1 and 5 equivalents with respect to compound (VIII).

5. The process according to claim 1, wherein the alkylation is carried out at a temperature between 0° C. and the boiling temperature of the solvent.

6. The process according to claim 5, wherein the alkylation is carried out at a temperature between 10 and 30° C.

7. The process according to claim 1, wherein compound (VII) is obtained by means of resolution of a racemic compound (V) comprising the following steps:

a') reaction of the racemic compound (V)

(V)

with a chiral acid in a polar solvent or mixture of polar solvents and subsequent precipitation of chiral salt (VI)

(VI)

b') treatment of the chiral salt (VI) with an aqueous basic solution to yield the compound (VII)

(VII)

c') extraction of the compound (VII) with an organic solvent.

8. The process according to claim 7, wherein the chiral acid is selected from D(−) mandelic acid, D(−) 2-chloromandelic acid, D(−) tartaric acid, and (2R,3R)-O,O'-dibenzoyl tartaric acid.

9. The process according to claim 8, wherein the chiral acid is D(−) mandelic acid.

10. The process according to claim 7, wherein the polar solvent of step a') is selected from: water, aliphatic ketones and/or aliphatic alcohols, used separately or in a mixture.

11. The process according to claim 10, wherein the aliphatic ketone is acetone and the aliphatic alcohol is selected from methanol, ethanol, 1-propanol and 2-propanol.

12. The process according to claim 10, wherein the polar solvent is a mixture of methanol and isopropanol.

13. The process according to claim 7, wherein the aqueous basic solution of step b') is an aqueous solution of ammonium hydroxide, an alkaline metal hydroxide or an alkaline-earth metal hydroxide.

14. The process according to claim 13, wherein the aqueous basic solution is an aqueous solution of sodium hydroxide or potassium hydroxide.

15. The process according to claim 7, wherein the organic solvent of step c') is selected from toluene, methyl tert-butyl ether, methyl iso-butyl ketone and 2-methyltetrahydrofuran.

16. The process according to claim 1, further comprising reaction of the compound (VIII) with an organic acid halide or anhydride to yield the compound (IX)

(IX)

wherein R is:
  $C_1$-$C_5$ alkyl, optionally substituted with 1-3 halogen atoms, or with a carboxyl group, optionally esterified with $C_1$-$C_4$ aliphatic alcohols, or,
  phenyl or benzyl, optionally substituted with 1-3 halogen atoms, with alkyl and/or carboxyl groups;
  or by reaction of the compound (VIII) with an organic acid and a dehydrating agent.

17. The process according to claim 16, wherein R is H, $CH_3$, $CH_2Cl$, $CF_3$, $CH_2CH_2COOH$, or $COOR^1$ wherein $R^1$ is H, $C_1$-$C_4$ alkyl, phenyl, chlorophenyl, or o-carboxyphenyl.

18. The process according to claim 16, wherein the dehydrating agent is selected from DCC (dicyclohexylcarbodiimide), HOBT (hydroxybenzotriazole), EDC (1-ethyl-3-(3-dimethylaminopropyl) carbodiimide) and T3P (2-propanefosfonic acid).

19. The process according to claim 16, wherein the organic acid halide or anhydride is selected from a halide or anhydride of a substituted or non-substituted aromatic or aliphatic organic acid.

20. The process according to claim 19, wherein the organic acid halide or anhydride is selected from a halide or anhydride of an $C_1$-$C_5$ alkyl acid, optionally substituted with 1-3 halogen atoms; a benzoic acid or a phenylacetic acid, optionally substituted with 1 to 3 halogen atoms, alkyl groups and/or carboxyl groups; $C_1$-$C_6$ dicarboxylic acids and their $C_1$-$C_4$ aliphatic esters.

21. The process according to claim 20, wherein the organic acid halide or anhydride is selected from a halide or anhydride of acetic acid, phenylacetic acid, chloroacetic acid, trifluoroacetic acid, benzoic acid, chlorobenzoic acid, phthalic acid, succinic acid, oxalic acid or $C_1$-$C_4$ aliphatic monoesters of oxalic acid or mixed formic acid anhydrides.

22. The process according to claim 21, wherein the organic acid halide or anhydride is trifluoroacetic acid.

23. The process according to claim 16, further comprising hydrogenation of the compound (IX) and subsequent aqueous solution hydrolysis to yield compound (X)

(X)

24. The process according to claim 23, wherein the hydrogenation is carried out in the presence of a catalyst and/or at a pressure between 1 and 100 bar and/or at a temperature between 0 and 100° C.

25. The process according to claim 24, wherein the catalyst is palladium on carbon.

26. The process according to claim 23, further comprising methylation of the compound (X) to yield the compound (XI)

(XI)

by using a methylating agent, optionally in the presence of a base, or by means of reductive methylation and a suitable reducing agent.

27. The process according to claim 26, wherein the reductive methylation is carried out by using formaldehyde, or a precursor thereof.

28. The process according to claim 26, wherein the methylating agent is selected from methyl iodide, methyl bromide, methyl chloride, dimethylsulfate, a sulfonic or benzenesulfonic acid methyl ester, substituted or non-substituted, and/or the base is an organic base or an inorganic base, and/or the reducing agent is selected from a hydride, hydrogen or a hydrogen donor.

29. The process according to claim 28, wherein the base is selected from triethylamine, diisopropylamine.

30. The process according to claim 28, wherein the reductive methylation is carried out in the presence of a catalyst.

31. The process according to claim 26, wherein the reductive methylation reaction is carried out by using formaldehyde and formic acid.

32. The process according to claim 26, further comprising O-demethylation of the compound (XI) to yield the tapentadol free base.

33. The process according to claim 32, further comprising crystallization of the tapentadol free base.

34. A process for the synthesis of tapentadol employing a compound of formula (VII')

(VII')

35. A process for the synthesis of tapentadol employing a compound of formula (VI')

(VI')

36. A process for the synthesis of tapentadol employing a compound of formula (VIII)

(VIII)

37. A process for the synthesis of tapentadol employing a compound of formula (IX)

(IX)

38. A process for the synthesis of tapentadol employing a compound of formula (X)

(X)

* * * * *